(12) United States Patent
O'Connor et al.

(10) Patent No.: US 6,364,481 B1
(45) Date of Patent: Apr. 2, 2002

(54) LENS WITH SURFACE CORRECTION

(75) Inventors: Kevin Douglas O'Connor, Goodwood; Anthony Dennis Miller, Bellevue Heights, both of (AU)

(73) Assignee: Sola International Holdings Ltd., Lonsdale (AU)

(*) Notice: Subject to any disclaimer, the term of this patent is extended or adjusted under 35 U.S.C. 154(b) by 0 days.

(21) Appl. No.: 09/341,153

(22) PCT Filed: Jul. 17, 1998

(86) PCT No.: PCT/AU98/00567

§ 371 Date: Aug. 20, 1999

§ 102(e) Date: Aug. 20, 1999

(87) PCT Pub. No.: WO99/04307

PCT Pub. Date: Jan. 28, 1999

(30) Foreign Application Priority Data

Jul. 18, 1997 (AU) .............................. PO 8090
Mar. 26, 1998 (AU) .............................. PP 2612

(51) Int. Cl.[7] .............................. G02C 7/02; G02C 7/10
(52) U.S. Cl. .................. 351/159; 351/41; 351/163; 351/44
(58) Field of Search ................. 351/159, 163, 351/41, 44

(56) References Cited

U.S. PATENT DOCUMENTS

| | | |
|---|---|---|
| 1,697,030 A | 1/1929 | Tillyer |
| 1,741,536 A | 12/1929 | Rayton |
| 1,942,400 A | 1/1934 | Glancy |
| 3,689,136 A | 9/1972 | Atamian |
| 3,691,565 A | 9/1972 | Galonek |
| 4,271,538 A | 6/1981 | Montesi et al. |
| 4,741,611 A | 5/1988 | Burns |
| 4,779,972 A | 10/1988 | Gottlieb |
| 5,187,505 A | 2/1993 | Spector |
| 5,648,832 A | 7/1997 | Houston et al. |
| 5,650,838 A | 7/1997 | Roffman et al. |
| 5,689,323 A | 11/1997 | Houston et al. |
| 6,036,315 A * | 3/2000 | Copeland .................. 351/159 |

FOREIGN PATENT DOCUMENTS

| | | |
|---|---|---|
| GB | 1509583 | 5/1978 |
| GB | 2 281 635 | 3/1995 |
| WO | 97/03579 | 2/1997 |
| WO | WO9741483 | 6/1997 |
| WO | 97/35224 | 9/1997 |

OTHER PUBLICATIONS

H. Callewaert, Communication including Supplementary European Search Report, Aug. 27, 1999, 3 pages.
M. J. Jestl, Communication Pursuant to Article 96(2) EPC, Apr. 3, 2001, 4 pages.

* cited by examiner

Primary Examiner—Scott J. Sugarman
(74) Attorney, Agent, or Firm—Burns, Doane, Swecker & Mathis, L.L.P.

(57) ABSTRACT

An optical lens element adapted for mounting in a frame of the wrap-around type, the lens element including a front and back surface capable of providing an optical zone (OZ), and a peripheral temporal zone (HT) which includes a surface correction to improve the overall field of vision of the wearer.

26 Claims, 9 Drawing Sheets horizontal section (y = 0)

vertical section (x=0)

LENS WITH SURFACE CORRECTION

FIELD OF THE INVENTION

The present invention relates to improvements to lenses for use in glasses of the wrap-around or shield type, such as sun-glasses, eye protection glasses, either clear or tinted, and safety glasses. While much of the following description, and indeed the description of the examples, will refer to piano lenses, it is to be understood that the lenses of the invention may also be of the prescription type.

BACKGROUND OF THE INVENTION

Glasses of the wrap-around or shield type traditionally provide for a very wide field of vision, and thus are often the preferred choice of glasses, be they sunglasses, safety glasses, or other forms of protective glasses, for sports, eye protection and the like. It is known in the prior an to manufacture piano (non-corrective) wrap-around glasses having wrap-around segments designed to shield the eye from incident light, wind, and foreign objects in the wearers field of temporal peripheral vision. Wrap-around frames for glasses of this kind, in the absence of lenses, would permit light to enter the eye from wide angles up to about 120° from the primary line of sight. However, prior art lenses for glasses of this type compromise the field of view afforded by the frames.

It has not been possible in traditional wrap-around glasses to avoid this diminished vision in the peripheral region. Thus, traditional wrap-around glasses often give rise to a reduced awareness of objects in the wearer's field of temporal peripheral vision (as a result of a reduction in the size of that field of vision). Additionally, such traditional wrap-around glasses often at least cause displacement of objects in a wearer's field of temporal peripheral vision, thus interfering with the wearer's peripheral perception of such objects.

Furthermore, such traditional wrap-around glasses typically also exhibit a degree of off-axis blur experienced with angles of gaze away from the primary line of sight.

It is an object of the present invention to provide lenses for use in glasses of the wrap-around type, which lenses will improve the wearer's field of peripheral vision and peripheral perception of objects, the improvement seeking to restore the wearer's field of peripheral vision and perception of objects to be closer to that when glasses are not being worm. The invention also aims to provide lenses which may advantageously, and additionally, reduce the off-axis blur in the optical zone thereof.

It is accordingly an object of the present invention to overcome, or at least alleviate, one or more of the difficulties and deficiencies related to the prior art.

The present invention provides an optical lens element adapted for mounting in a frame of the wrap-around type, the lens element including a front and back surface capable of providing an optical zone, and a peripheral temporal zone which includes a surface correction to improve the overall field of vision of the wearer.

The optical lens element according to the present invention thus provides the wearer, in the peripheral temporal zone, with an increased awareness of objects and a substantially improved perception of the correct object location. The overall field of vision may thus increase for example by up to approximately 2.3°, where the surface correction fully compensates for prismatic errors in the peripheral temporal zone.

Preferably, the lens element in the optical zone further includes a first correction to enhance vision by reducing the off-axis blur, and/or a second correction in the optical zone to assist in ensuring that the primary line of sight is undisturbed. Both of these further preferred corrections will be described below.

The optical zone of the lens element is the zone where it is intended to provide generally clear foveal vision as the line of sight of the eye rotates about its primary ('straight ahead') direction, as it would during typical eye movements. In this respect, it is desirable that the optical zone will include at least those portions of the lens that are used during eye rotations of up to 50° on the temporal side, up to 45° on the nasal side, and up to 30° vertically up and down from the primary (straight ahead) line of sight, with the lens in the as-worn position.

The optical zone will preferably be piano (or of zero refractive power), and the following description of preferred embodiments of the present invention will generally only describe a piano configuration. However, it will be appreciated that the optical zone may be of a prescription power of minus or plus power. In this respect, the optical zone of the optical lens element of the present invention may generally be described as including a prescription or Rx zone. The embodiment where the optical zone is piano may then be considered as a specific case thereof (Rx of zero power). The ophthalmic lens element may thus be a piano lens (or of zero refractive power), or a lens of negative or positive refractive power.

Before turning to describe the various preferred features of the lens element of the present invention, it should also be appreciated that the term 'optical lens element' refers to a finished optical or ophthalmic lens, or a laminated lens formed from a pair of lens wafers which may be utilised in the formation of an optical lens product. In this respect, where the optical lens element includes an ophthalmic lens wafer, the peripheral temporal zone may be provided by the front wafer or the back wafer. The ophthalmic lens may include a spherical, aspheric, toric, atoric, surface or any combination thereof and may exhibit an astigmatic correction. Further, the optical lens element may be a single vision, bi-focal or progressive lens.

Applicants have discovered that it is possible to provide an extended field of vision in a lens of the wrap-around type, whilst permitting the lens to form an optical zone, and yet still to provide a lens which provides a shield in the area of the temples. This is achieved by having a surface correction in the peripheral temporal zone.

In relation to this surface correction, beyond the optical zone (on the peripheral temporal side of the lens element), the horizontal component of prism (as assessed normal to one of the lens surfaces) preferably varies smoothly from base-nasal values, which are characteristic of the optical zone, to base temporal values, which are characteristic of those regions of the lens element of the present invention which are used for extreme temporal peripheral vision. This is in contrast to existing piano lens elements where the prismatic power continues to increase in the base-nasal sense towards the periphery of the lens element.

The preferred nature of the surface corrections may be easily understood by defining a meridian on a lens element and referring to prism in relation to it. Thus, consider a meridian on a lens element, the meridian being horizontal when the lens element is in the as-worn position, and the meridian passing through the lens centre. Then, consider the horizontal component of prism (as measured normal to one of the lens surfaces) at points along this meridian which lie between the lens centre and the temporal limit of the frame.

Preferably, the value of this horizontal component of prism at the point of intersection of the line of sight of the wearer and the lens surface will be either near zero or in a base-nasal direction. Regardless, this prism component preferably varies continuously along the meridian, and attains a maximum value in a base-nasal direction at some point along the meridian. In the preferred form the point of maximum base-nasal prism will be at, or near, the boundary of the optical zone.

Then, as mentioned above, on the peripheral temporal side of the lens element, beyond the point of maximum base-nasal prism, the horizontal component of the prism (as measured normal to one of the lens surfaces) preferably reduces smoothly in value to at least 0.1 prism dioptre less, more preferably at least 0.25 prism dioptre less than the maximum value.

In a further preferred embodiment the horizontal component of the prism reduces smoothly from the maximum base-nasal prism value an amount in the range of 0.1 to 2.5 prism dioptre, at the temporal extremity of the lens element.

Preferably the reduction in base-nasal prism is in the range of 0.75 to 2.0 prism dioptre, more preferably in the range of 1.3 to 1.9 prism dioptre.

The horizontal component of prism may reduce to a substantially zero value or may reach base-temporal values.

Thus, in the as-worn position, the level of prism at the extreme limit of vision, e.g. at the edge of the frame, is reduced to substantially zero.

The prismatic effect of the lens in the temporal peripheral region is assessed by the eye with the lens in the as-worn position in terms of light rays entering the entrance pupil which is close to the position of the iris immediately at the front of the crystalline lens within the eyeball.

This is the effective aperture stop through which light from extreme temporal peripheral regions passes before sensing by the retina.

Referenced from the entrance pupil the level of horizontal component of prism achieves maximum values in a base-nasal direction at or near the boundary of the optical zone. In the region on the temporal side of the optical zone, the horizontal component of prism may reduce smoothly to lower base-nasal values, substantially zero or to base-temporal values.

Alternatively, beyond the point of maximum base-nasal prism, the horizontal component of the prism remains substantially constant, namely meaning a prism value to within ±0.1 prism dioptre.

It has surprisingly been found that whilst a prism correction in the temporal peripheral zone may substantially fully compensate for prismatic errors, the wearer, in use, may be aware of a disturbance in their object field.

It is accordingly preferred that the placement and/or degree of application of the peripheral prismatic correction is such that any perception by wearers of peripheral image distortion or motion/vestibular effects, is reduced or eliminated.

The experience of wearers has revealed that a small percentage of cases report negative reactions to application of base-out prism if the changes encroach too closely on the optical zone (or the region traversed by the line of sight during extreme eyeturn) and/or the degree of surface modification is too large or too rapid.

In order to reduce or eliminate any possibility that the most sensitive wearers could experience disturbed visual fields it is preferable to displace the surface modification further temporally and/or reduce the degree of, or rate of change of, horizontal peripheral prism.

For example the start point of the surface modification may be 22.5 mm (or 57 degrees of eyeturn). Alternatively, or in addition, the degree of prismatic correction may be reduced to less than 100%, preferably approximately 80% to 95% of that required to fully eliminate prismatic error at the extreme limit of the field of vision.

In a further preferred form of the present invention, the front and/or back surface of the optical lens element may further include a surface correction to at least partially compensate for prismatic errors in theprimary line of sight (the zone of 'straight-ahead' vision). Preferably, the surface correction may be a prismatic correction. More preferably, the prismatic correction may be a base-in or base-nasal correction applied to the front and/or back surface.

Indeed, in a preferred form of the present invention, the front and back surfaces of the lens element are preferably both tilted with respect to one another at the lens centre. This tilt is preferably such that when the lens is in the as-worm condition, the primary line of sight undergoes no angular deviation in a horizontal plane as it passes through the lens. Typically, this will require that the back surface be tilted relative to the front surface by approximately 0.4° towards the nasal side of the lens, resulting in a base-nasal prism of approximately 0.4 dioptre when assessed normal to the surfaces. This value of tilt will of course depend upon various factors such as lens form, frame tilt and lens material.

For example, base-temporal prismatic errors for straight ahead vision which are a consequence of oblique viewing through tilted highly curved lens surfaces may be corrected with such base-nasal prism—typically 0.4 prism dioptre for an 8 base lens element, formed from polycarbonate and exhibiting 1.8 mm centre thickness and 20° wrap.

With this in mind, it will be appreciated that in one form the present invention thus includes a configuration where two prismatic corrections are provided, one in relation to the primary line of sight and one in relation to temporal peripheral vision.

Furthermore, the front and/or back surfaces of the lens element in the optical zone may be atoric, aspheric, toric or spherical, or any other complex form. An aspheric or atoric surface may be chosen so as to minimise the off-axis optical astigmatism, any errors in off-axis optical power from piano, or indeed to minimise any off-axis blur which is derived from such astigmatic or power errors. Typically, this will result in a back surface curve which becomes flatter, or a front surface curve which becomes steeper away from the lens centre.

In summary, and in relation to the peripheral regions of the lens element of the present invention, it Will be appreciated that light entering obliquely through the highly curved surfaces introduces a base-nasal prism, which in turn has the consequence of reducing the wearer's field of view. In this respect, in some prior art wrap-around lenses, there would be a field loss in each eye of approximately 2.3° from some 4 dioptre of prism with a typical piano extension. However, in contrast the optical lens element of the present invention reduces the abovementioned field loss without compromising the optical performance of the lens in the optical zone. Furthermore, other preferred embodiments of the present invention additionally introduce corrections to enhance vision in the optical zone by reducing the off-axis blur, and to ensure that the primary line of sight is undisturbed, thus reducing eyestrain.

Alternatively, in another form of the invention, the front surface of the lens element is preferably capable of being mounted in a frame of constant design curve of between 6.00 D and 12.00 D or more, but preferably between 8.00 D and 9.00 D. Further, the front surface of the lens element may have a high curve extending from nasal to temporal limits, but the vertical curve is preferably 6.00 D. or below. Thus, it will be understood that such vertical curves permit final lenses, preferably edged lenses, to be adapted to the shape of the wearer's face and so locate closely in a form of the wrap-around type (a so-called "toric" design).

Further, in order to create an effectively larger diameter lens blank suited to wrap frames which extend toward the temporal edge, the design centre can be decentred on the lens blank some distance nasally from the lens geometric centre, for example around 10 mm. This places the design centre near the viewers normal forward line of sight, at the same time preserving adequate lens material on the temporal edge to fill the frame.

The optical lens elements of the present invention may be provided in various forms, such as in the form of a unitary lens adapted for mounting in a frame of the wrap-around type.

In a particularly preferred embodiment, the present invention may also provide a spectacle frame, or a unitary lens, having a pair of optical lens elements, which lens elements provide true correction in an optical zone for a wearer up to 50° off axis, and terminating in a peripheral temporal zone. This particularly preferred embodiment improves a user's perception of objects in their peripheral vision area, the improvement aiming to restore that vision to normal (i.e. when not wearing glasses at all).

In a further aspect of the present invention, there may be provided an optical lens element adapted for mounting in a frame of the wrap-around or shield type, such that the lens element is rotated temporally about a vertical axis through the design centre thereof, the lens element including a front and back surface capable of providing an optical zone, and a peripheral temporal zone including a surface correction to improve the overall field of vision of the wearer, the front and/or back surface bearing a surface correction to at least partially adjust for errors including astigmatic and power errors.

In a preferred aspect of the present invention, as stated above, the optical lens element may be formed as a laminate of a front and back lens wafer.

Accordingly, in a preferred aspect of the present invention, there is provided a laminate optical article adapted for mounting in a frame of the wrap-around or shield type, including a front lens wafer, and
a complementary back lens wafer; the front and back lens wafers of the laminate optical article defining.
an optical lens element including
  a front and back surface capable of providing an optical zone and a peripheral zone;
  the front and/or back surface in the peripheral temporal zone bearing a prismatic correction such that the horizontal component of prism varies smoothly from base-nasal values to substantially zero across the zone;
  the front and/or back surface in the optical zone bearing a base-nasal prismatic correction to at least partially compensate for prismatic errors in the primary line of sight of the wearer in the as-worn position.

Preferably the front and/or back surface further includes a surface correction to at least partially adjust for optical errors including astigmatic and mean power errors The ophthalmic lens may be formulated from any suitable material. For example, a polymeric or glass material may be used. The polymeric material may be of any suitable type. The polymeric material may include a thermoplastic or thermoset material. A material of the diallyl glycol carbonate type, e.g. CR-39 (PPG Industries) may be used. Alternatively, a polycarbonate material may be used.

In a further aspect of the present invention, there is provided a method-of designing an optical lens element adapted for mounting in a frame of the wrap-around or shield type, which method includes providing
  a mathematical or numerical representation of a first surface of an optical lens element including a section designed to provide the desired prescription (Rx) in the optical zone, and
adding thereto
  a mathematical or numerical representation of a peripheral temporal zone; and
  a mathematical or numerical representation of a transition section designed to smoothly blend the prescription zone and peripheral temporal zone to define a complete lens surface; and
modifying the representation of the lens surface to introduce a prismatic correction in the peripheral temporal zone to improve the overall field of vision of the wearer.

In a preferred aspect, the method may further include
modifying the representation of the lens surface in the optical zone to provide a prismatic correction in the optical zone such that the primary line of sight undergoes substantially no angular deviation in a horizontal plane as it passes through the lens element.

In a further preferred aspect, the method may still further include
providing a mathematical or numerical representation of a second surface of an optical lens element including a section designed to provide the desired prescription (Rx) in the optical zone, and optionally adding thereto a mathematical or numerical representation of a peripheral temporal zone to define a second complete lens surface;
optionally rotating and/or decentring the representation of the lens surface(s) to permit mounting in a suitable frame, and
modifying the representation of the lens surface(s) to at least partially adjust for induced optical errors in the peripheral zone and optical zone including astigmatic and mean power errors.

In relation to these methods, it will be appreciated that reference to "the desired prescription (Rx) in the optical zone" includes a prescription of zero power for the preferred piano embodiment. In this respect, where a lens element in accordance with the present invention does have a power other than zero, it will be appreciated by a skilled addressee that consequent minor alterations may need to be made to the configurations described herein.

DETAILED DESCRIPTION OF PREFERRED EMBODIMENTS

The present invention will now be more fully described with reference to the accompanying figures and examples. It should be understood, however, that the description following is illustrative only and should not be taken in any way as a restriction on the generality of the invention described above.

Figure 8:
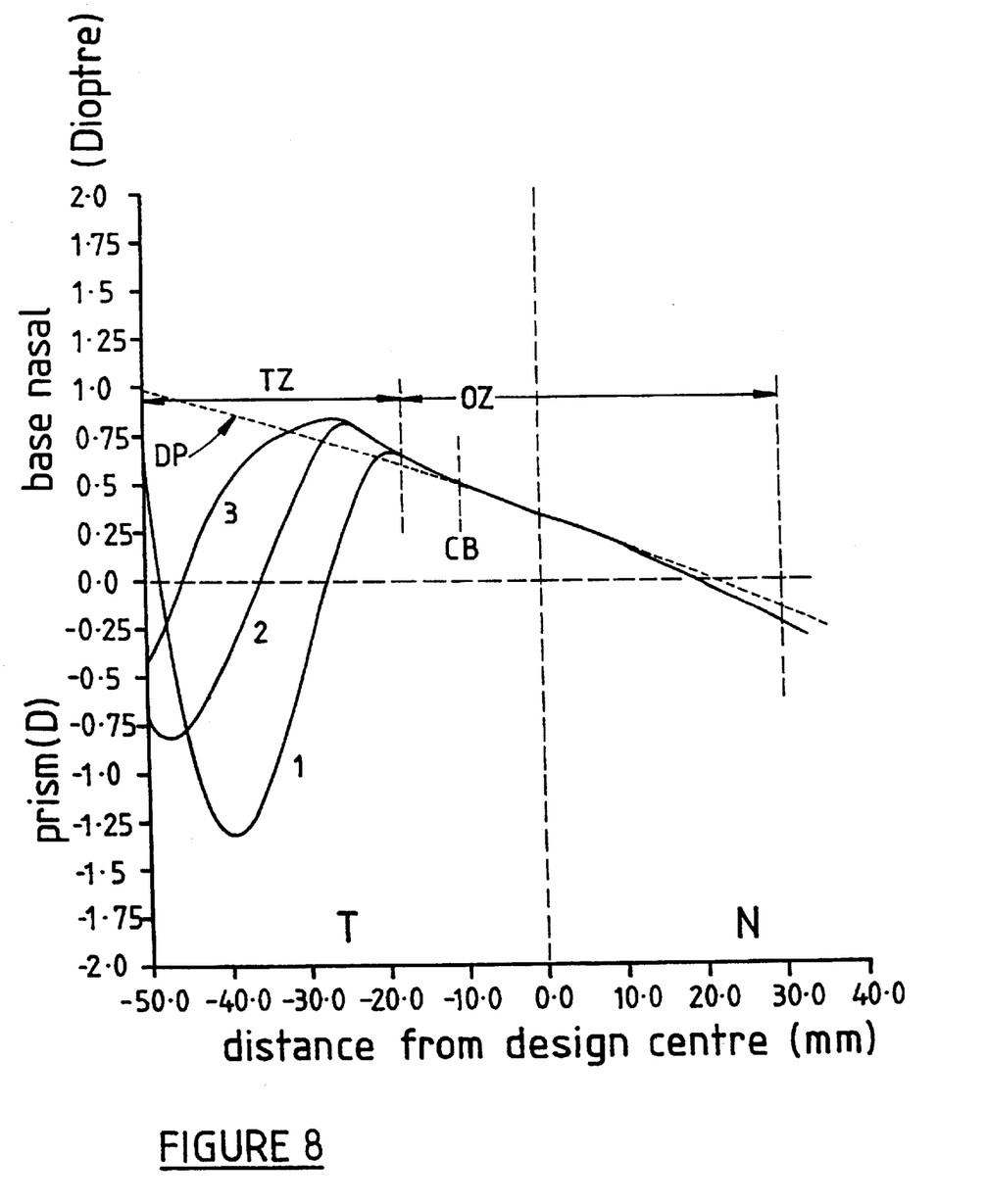
FIG. 8 is a graph showing horizontal prism along the temporal-nasal axis as measured normal to the front surface.

In more detail, FIG. 8 illustrates how horizontal prism varies across a series of lens elements according to the present invention.

The dotted line DP represents horizontal prism for a typical prior art decentred piano lens for which a simple correction has been made for prismatic deviation from straight ahead vision. In both cases, the horizontal component of prism is seen to continue to increase (at approximately a fixed rate) in the base-nasal direction outside the optical zone as the distance from the lens centre increases on the temporal side.

OZ represents the optical zone of the lens elements according to the present invention.

TZ represents the peripheral temporal zone of the lens elements according to the present invention.

CB represents the centre of the lens blank.

It will be seen that the embodiments represented by graphs 1, 2 and 3 deviate from a typical decentred piano DP in particular in the peripheral temporal (T) zone where prism reduces smoothly and rapidly from base-nasal values to zero or to base-temporal values.

Figure 9:
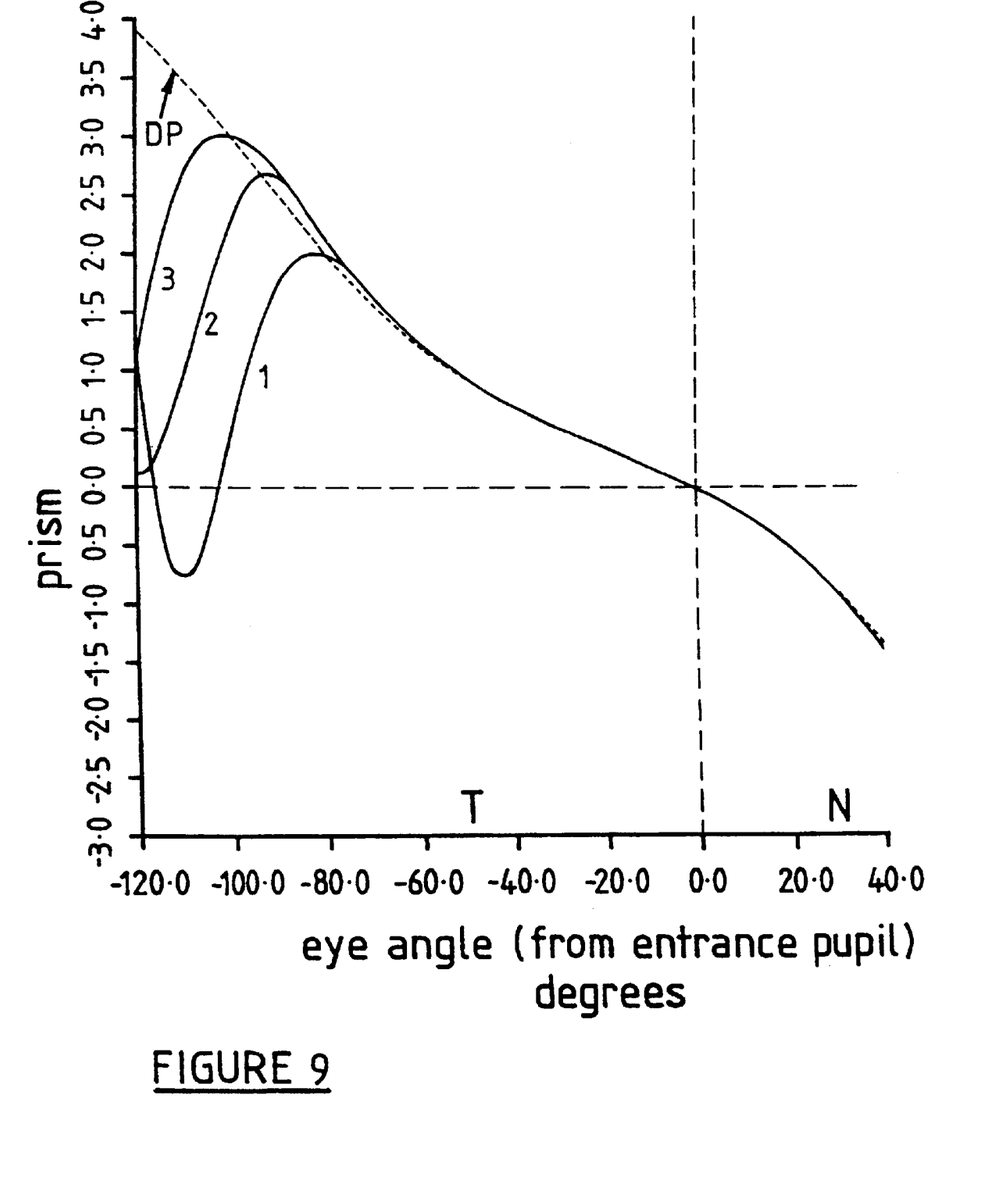

As best seen in FIG. 9, graph 1 illustrates the case where peripheral prismatic deviation referenced to the entrance pupil is reduced to substantially zero (or below).

Applicants have discovered, however, that this substantially complete prismatic correction may lead to a disturbance in the object field of the wearer at the extreme periphery of vision. Thus a less than complete prismatic correction, as illustrated in graphs 2 and 3, may be preferred in some circumstances.

Figure 7:
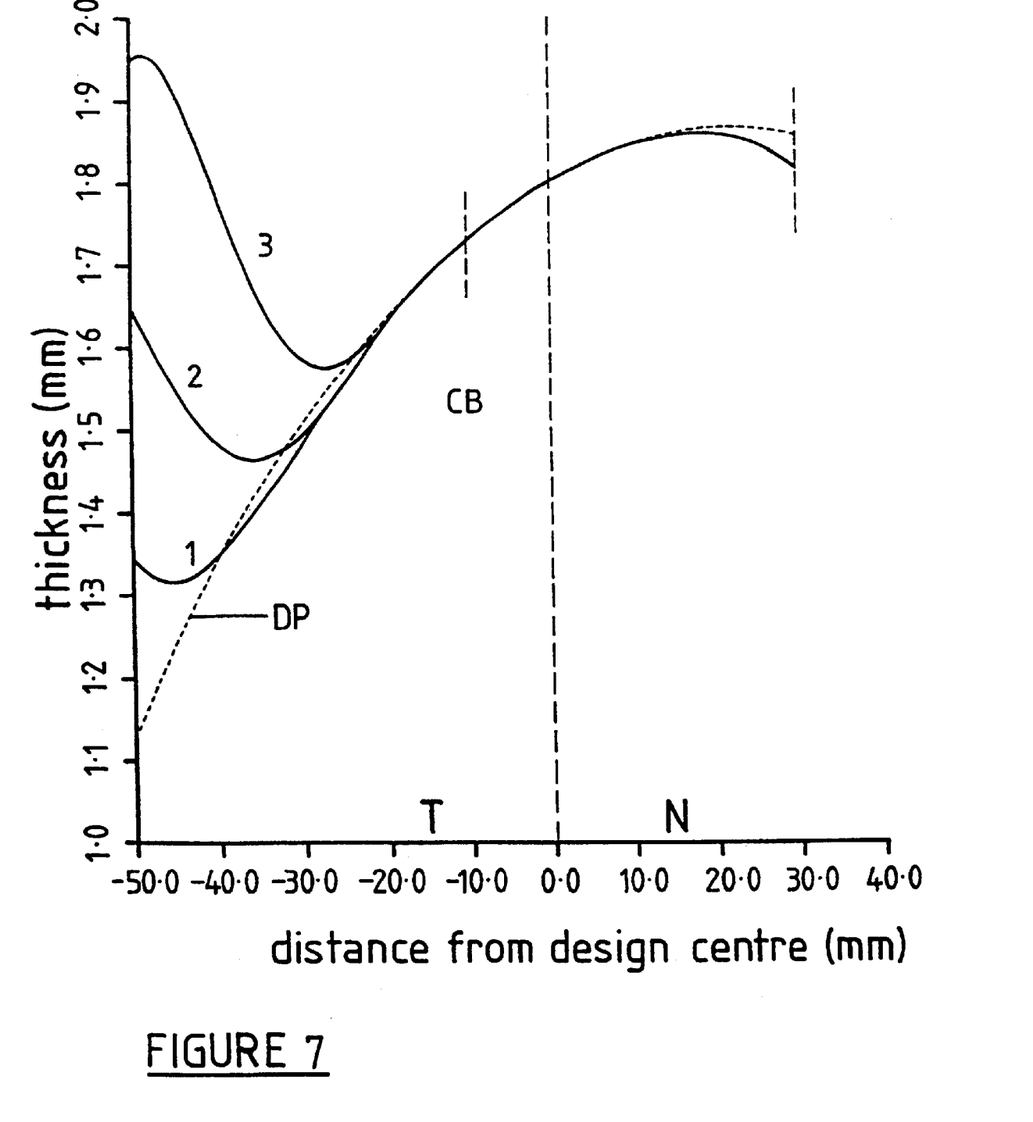
FIG. 7 is a graph of horizontal section thickness (normal to the front surface) versus distance from the design centre of the lens.

Similarly, as best seen in FIG. 7, the prism correction in the peripheral temporal zone is represented by a slight increase in thickness of the lenses relative to a typical decentred piano DP towards the periphery thereof. This is advantageous for fitting purposes as the lens has a more uniform edge thickness and so is more robust and thus less inclined to warp or break during the edging process.

EXAMPLE

The following example describes a generally piano lens with a prism modified periphery which reduces the loss of a wearer's peripheral field of view. The example relates to a lens which is made out of a material of a refractive index of 1.586.

1. The front surface is convex spherical with a radius of curvature of 65.43 mm.

Figure 1:
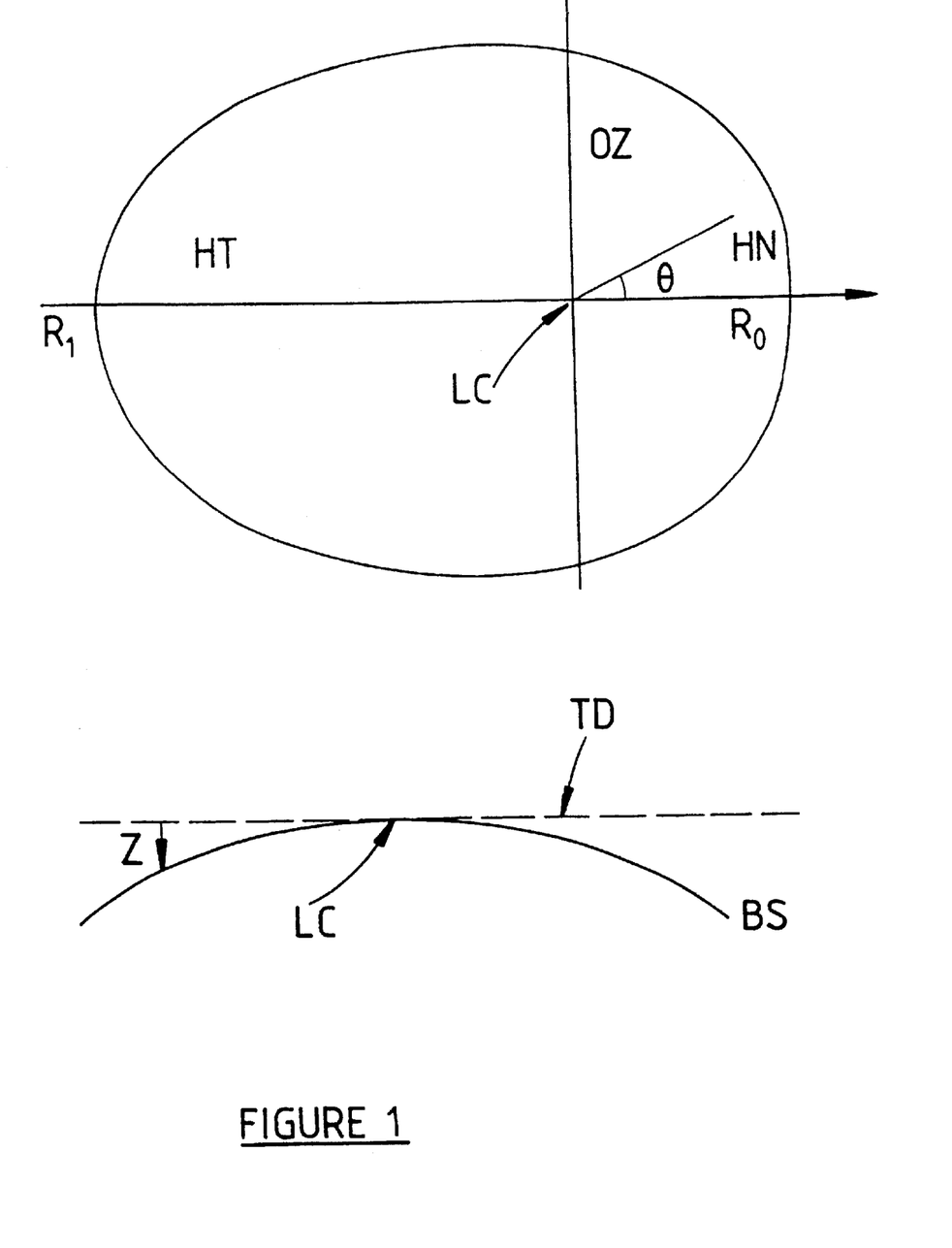
FIG. 1 is a schematic representation of lens coordinates referred to in the example.

2. The back surface is concave. It may be conveniently described in terms of its perpendicular distance z from the tangent plane (TP) of the back surface (BS) at the lens centre (LC). Let $$z = z(r, \theta)$$

where r, θ are polar coordinates in the plane (see FIG. 1). The θ=0 axis corresponds to the nasal side of the horizontal axis (HN) of the lens in the as-worn configuration, and the θ=π corresponds to the temporal side.

3. The optical zone is defined as the region of the lens described by $$0 \leq r \leq R, \text{ where } R(\theta) = R_1 + \tfrac{1}{2}(R_0 - R_1)(1 + \cos\theta)$$

In this formula, $R_0$ and $R_1$ are the radial limits of the optical zone (OZ) in the nasal (N) and temporal (T) regions respectively. A convenient choice is R0=27.5 mm, and $R_1$=17.5 mm 4. Within the optical zone, a convenient choice for z(r,θ) could be $$z(r, \theta) = \sum_{j=1}^{3} \sum_{k=0}^{k=j} C_{j,k} r^{2j} \cos^{2(j-k)}\theta \sin^{2k}\theta$$

where the coefficients $c_{j,k}$ are given in the following table:

| $c_{j,k}$ | k=0 | k=1 | k=2 | k=3 |
|---|---|---|---|---|
| j=1 | 0.772923-02 | 0.77249E-02 | | |
| j=2 | 0.41249E-06 | 0.81742E-06 | 0.4063E-08 | |
| j=3 | 0.49748E-10 | 0.95916E-10 | 0.21102E-09 | 0.59706E-10 |

5. Outside the optical zone, z may be conveniently described in the form of a polynomial in the radial coordinate r, $$z(r, \theta) = a(\theta) + b(\theta)(r - R(\theta)) + c(\theta)(r - R(\theta))^2 + d(\theta)(r - R(\theta))^3 \text{ for } r \geq R(\theta)$$

Using well known mathematical techniques, it may be shown that the requirement that z and the first and second partial derivatives of z with respect to r, each be continuous across the optical zone boundary r=R(θ), will uniquely determine the values of the coefficients a(θ), b(θ) and c(θ). The coefficient d(θ) remains unassigned, and may be used to achieve the desired prismatic behaviour.

A convenient way to proceed is to require that z attain a prescribed value at a specified radius r=R∞ say. In particular, the following choices may be made:

$$R\infty = 42.5 \text{ mm}$$

$$z(R\infty\theta) = S_1 + \tfrac{1}{2}(S_0 - S_1)(1 + \cos\theta)$$

where $$S_0 = 16.00 \text{ mm, and } S_1 = 16.75 \text{ mm.}$$

Here $S_0$ and $S_1$ represent the surface heights at R∞ on the nasal and temporal sides respectively. From this requirement, the coefficient $d(\theta)$ may then be determined using standard mathematical techniques.

It will be understood, however, that the lines of sight of the two eyes of the wearer would need to be directed inwards (each by the angle $\psi$) so as to form a single image of a straight ahead, distant object. This would usually be considered an undesirable condition, as it leads in many individuals to headaches, eye strain and other forms of visual discomfort.

The front and back surfaces are positioned relative to one another so that at the design centre, the normals to the two surfaces make an angle of 0.32 degrees to each other in the horizontal plane in such a manner to create base-nasal prism. The thickness of the lens at the lens centre, measured normal to the front surface, should be for example 1.8 mm.

The lens should be mounted in a wrapped frame and worn in such a manner that the primary ('straight ahead') line of sight intersects the back surface at the design centre, and makes an angle with the normal to the back surface at that point of 20 degrees in the horizontal plane. The lens is then subjected to a straight ahead prism correction in known manner. For a typical 8 D lens, a prismatic correction of approximately $0.36^\Delta$, base nasal may be required.

1. Peripheral Prismatic Deviation

This example describes the prismatic errors and associated loss of field of view with a typical prior art decentred piano lens. It further shows the manner of improvement in the field of view and reduction in the blind spot at a typical temporal wrap frame limit of 115° measured from the entrance pupil. The entrance pupil, estimated typically 13 mm behind the eyeside surface of the lens, is the appropriate point of entry into the eye of rays entering from the far peripheral area when the direction of gaze is directly forward.

Figure 2:
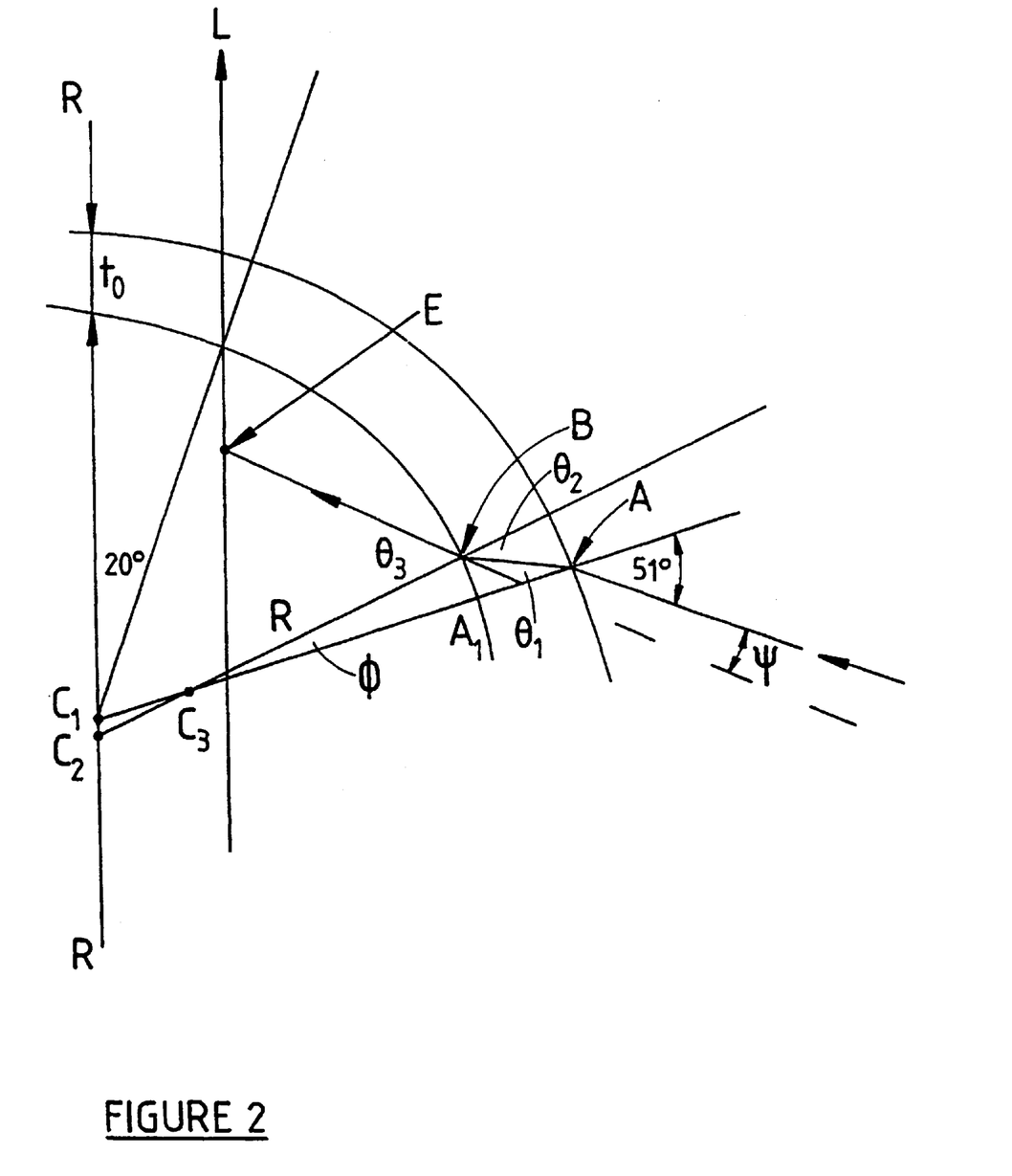
FIG. 2 is a schematic representation of lens parameters referred to in the example.

With reference to FIG. 2, this is a spherical decentred prior art lens having the following characteristics:

$R=C_2B$ 66.25mm Surfaces of lens with centres $C_1$ for front surface and $C_2$ for back surface.

$C_1C_2=1.1$ mm $t_0$=lens thickness=1.8 mm

M=material refractive index=1.586

E=entrance pupil of the eye

EL=line of sight

A=point of entry of ray at typical frame limit $\psi$=angle exit ray makes with incoming ray Consider a ray from a distant object which intersects the front surface at A at a typical angle of incidence of 51° referenced to the surface normal $C_1A$.

After refraction at A $$\theta_1 = \arcsin\left(\frac{\sin 51}{1.586}\right) = 29.34°$$

The ray is refracted to the point B on the eyeside surface.
The surface normal at B is different from that at A by the angle $\phi$.

$$\phi = \arctan\left(\frac{t_0\tan\theta_1 + C_1C_2}{R}\right)$$
$$= \arctan\left(\frac{1.8\tan 29.34 + 1.1}{66.25}\right)$$
$$= 1.82°$$

Angle of incidence at B $$\theta_2 = (\theta_1 + \phi)$$
$$= (29.34 + 1.82)$$
$$= 31.16°$$

After refraction at B $$\theta_3 = \arcsin 1.586\sin 31.16$$
$$= 55.14°$$

$\psi$ = angle the refracted ray at $B$ exists relative to the incoming ray at $A$.

$$\psi = (\theta_3 - \phi) - 51$$
$$= (55.14 - 1.82) - 51$$
$$= 2.32° \text{ base nasal}$$

This is the effective angle of deviation of an incoming ray caused by the lens.

The prismatic effect is $\Delta=100 \tan \psi$ $\Delta=4.0 \Delta$ base nasal

Figure 5:
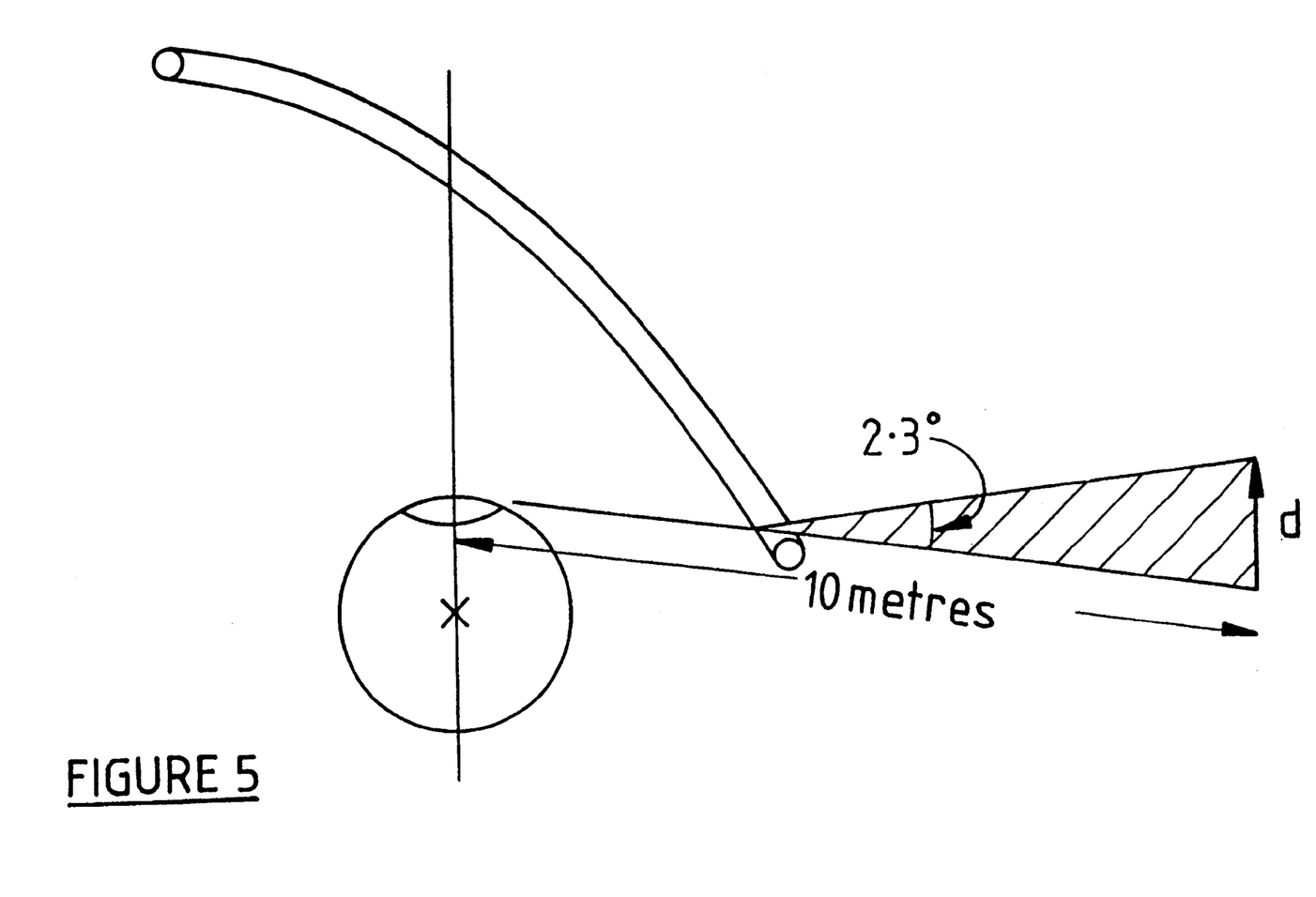
FIG. 5 illustrates the prismatic displacement of objects where loss of field is approximately 2.3°.

This creates an effective blind region (d) of size 40 cm at a distance of 10 m (FIG. 5).

Lens of Present Invention

With reference again to FIG. 2, the lens eyeside surface is adjusted to create base-out prism (measured normal to the lens surface).

Again, for example at the typical temporal edge of the frame, the eyeside surface is rotated at B in the direction of base-out prism by 0.95°.

The incident angle at B now becomes $$\theta_2 = 31.16 - 0.95 = 30.21°$$
$$\theta_3 = \arcsin 1.586\sin 30.21°$$
$$= 52.94°$$
$$\psi = (\theta_3 - \phi) - 51$$
$$= 0.12° \text{ base nasal.}$$

The angle of deviation is equivalent to $100 \tan 0.12 = 0.21\Delta$ of base nasal prism.

Figure 3:
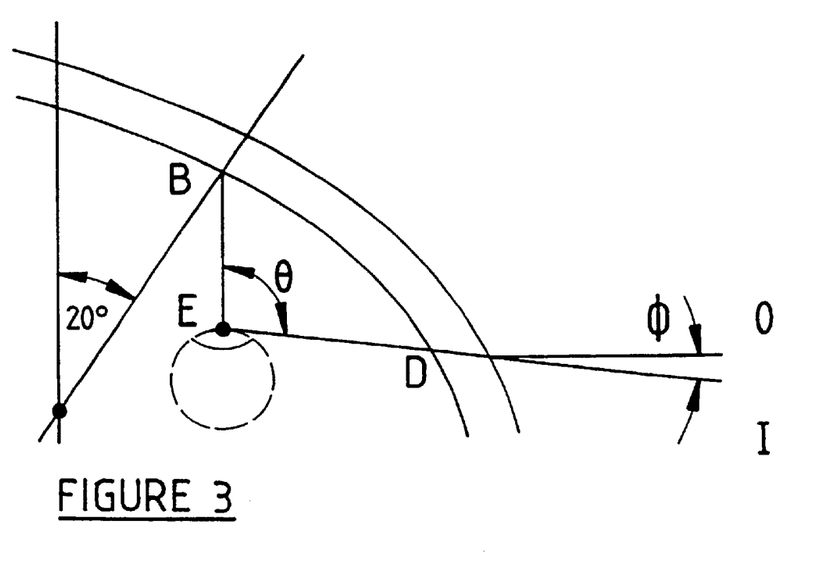
FIG. 3 is a schematic illustration of a piano lens element, illustrating a loss of visual field at angle φ in the peripheral zone, the entrance pupil E of the eye, the back vertex B of the lens, and the angle θ (on the eye side) of a peripheral ray relative to the straight ahead foveal direction of gaze.
Figure 4:
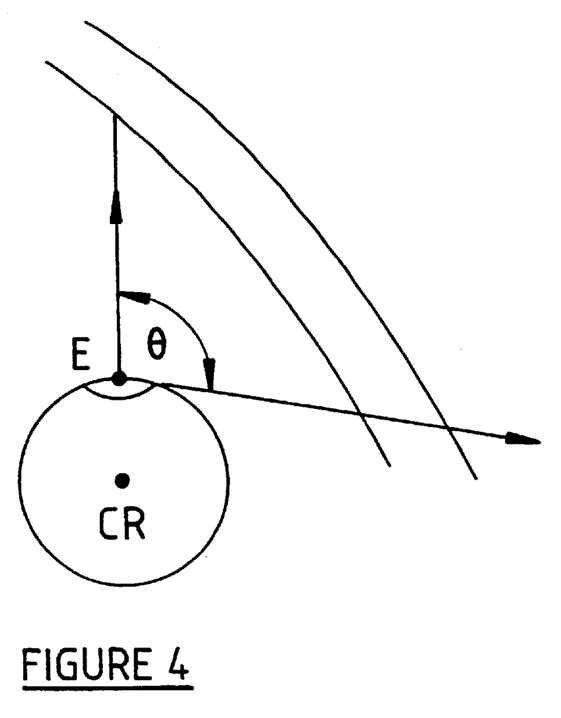
FIG. 4 illustrates how the angle of vision B is measured relative to the entrance pupil of the eye.

With the lens worn in the configuration illustrated in FIGS. 3 and 4, the peripheral prismatic values, angle of deviation of incoming ray and displacement of objects at 10 m distant are shown. The field of view improvement and reduction of the displacement of objects at the blind spot is also shown.

The values are for the example above at incident ray angles of 115° to the entrance pupil.

|  | Prism measurement normal to surface | Prism measurement from entrance pupil | Angle of ray deviation - lost field of view | Displacement of objects at 10 m distant |
|---|---|---|---|---|
| Standard spherical decentred lens (prior art) | 0.9 base nasal | 4.0 Δ | 2.3° | 40 cm |
| Lens of present invention | 0.8 base temporal | 0.25 Δ | 0.1° | 2.5 cm |
| Improvement |  |  | 2.2° | 37.5 cm |

Referring to FIG. 5, a 3 prism dioptre prismatic deviation, corresponding to a field loss of 2.3°, is characteristic of existing piano lenses at 115° of temporal eye angle. For an object distance of 10 metres, the value of d (displacement of object) is 40 cm. This displacement is brought effectively to zero after peripheral prism correction in accordance with the present invention.

2. Calculation of Surface of Optical Lens Element

For a lens having a front sphere having of 8.00 D and a back asphere, the following holds:

| Radius (mm) | Mean surface power of back surface | |
|---|---|---|
|  | H (dioptre) | V (dioptre) |
| 0 | 8.09 | 8.09 |
| 5 | 8.09 | 8.08 |
| 10 | 8.06 | 8.05 |
| 15 | 8.02 | 8.01 |
| 20 | 7.96 | 7.96 |
| 25 | 7.88 | 7.90 |

For a lens having a back sphere having 8.09 D and a front asphere, the following holds:

| Radius (mm) | Mean surface power of front surface | |
|---|---|---|
|  | H (dioptre) | V (dioptre) |
| 0 | 8.00 | 8.00 |
| 5 | 8.01 | 8.01 |
| 10 | 8.03 | 8.04 |
| 15 | 8.07 | 8.08 |
| 20 | 8.13 | 8.12 |
| 25 | 8.19 | 8.15 |

Figure 6A:
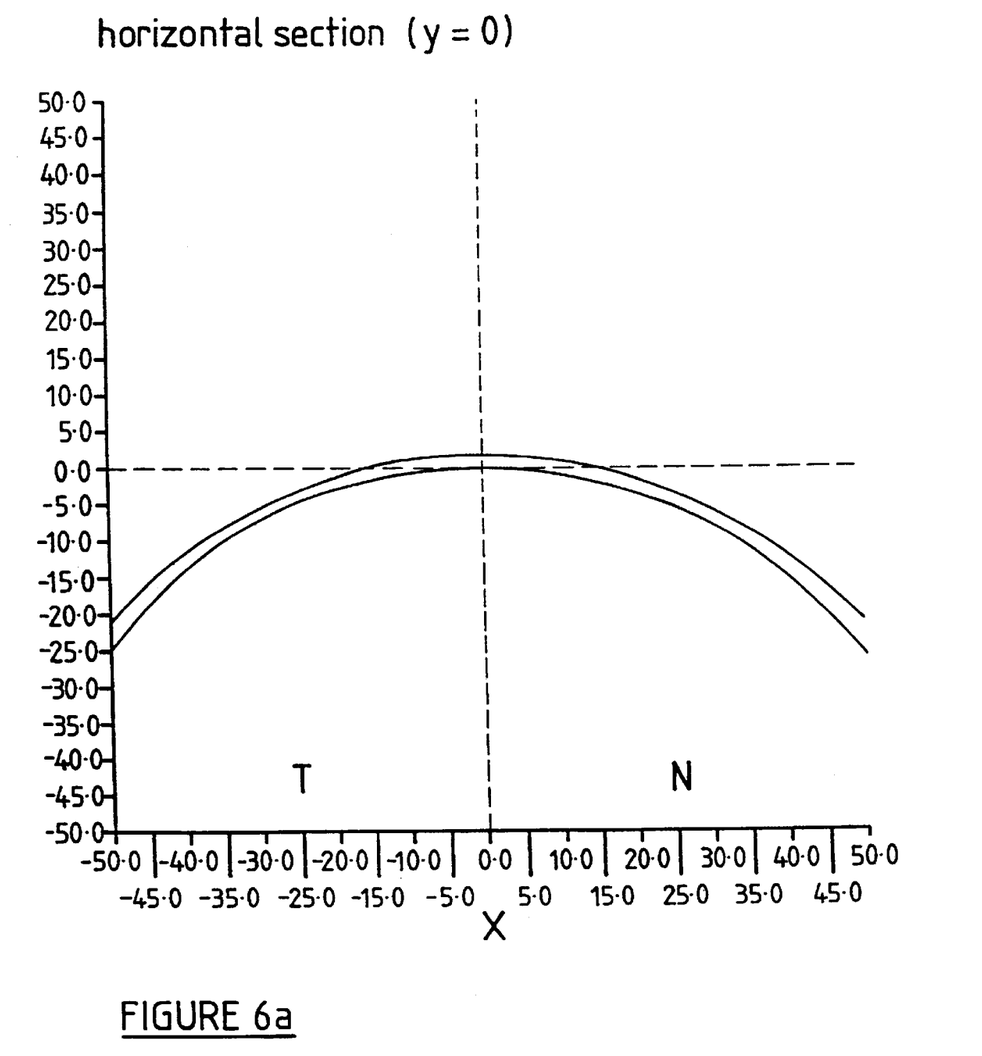
FIG. 6a is a horizontal section through an optical lens element according to the present invention.
Figure 6B:
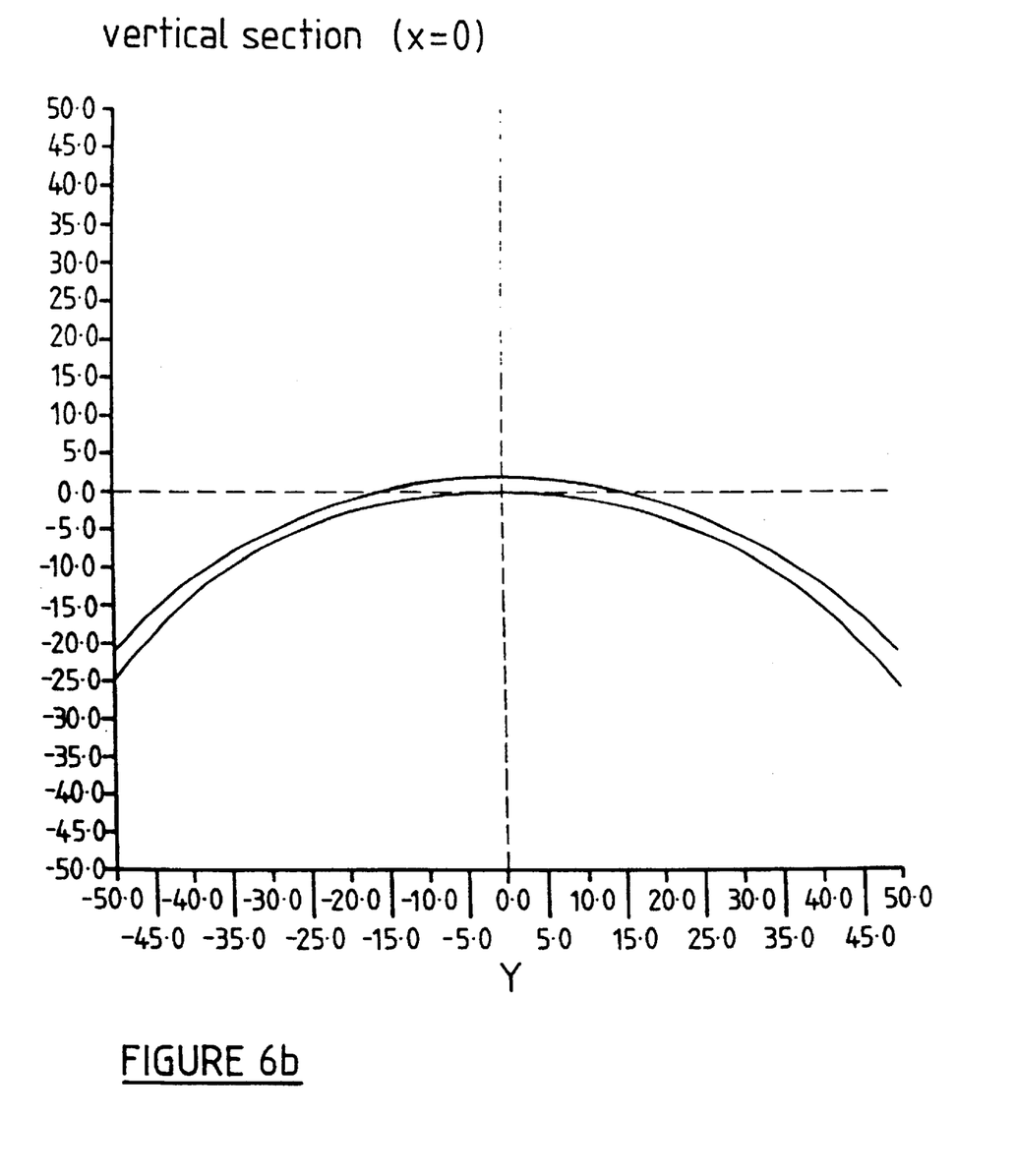
FIG. 6b is a vertical section through an optical lens element according to the present invention.

3. Finally, Cartesian co-ordinates for the horizontal and vertical sections for an optical lens element according to the present invention are set out below. The horizontal and vertical sections so defined are illustrated in FIGS. 6a and 6b respectively.

| Horizontal Section | | | | |
|---|---|---|---|---|
| x | y | z-thick | z-front | z-back |
| −50.000 | 0.000 | 3.611 | −20.987 | −24.597 |
| −40.000 | 0.000 | 2.240 | −11.638 | −13.879 |
| −30.000 | 0.000 | 1.698 | −5.382 | −7.080 |
| −20.000 | 0.000 | 1.699 | −1.291 | −2.990 |
| −10.000 | 0.000 | 1.746 | 1.041 | −0.705 |
| 0.000 | 0.000 | 1.800 | 1.800 | 0.000 |
| 10.000 | 0.000 | 1.870 | 1.041 | −0.829 |
| 20.000 | 0.000 | 1.956 | −1.291 | −3.247 |
| 30.000 | 0.000 | 2.112 | −5.382 | −7.494 |
| 40.000 | 0.000 | 2.880 | −11.638 | −14.518 |
| 50.000 | 0.000 | 4.630 | −20.987 | −25.617 |

| Vertical Section | | | | |
|---|---|---|---|---|
| x | y | z-thick | z-front | z-back |
| 0.000 | −50.000 | 4.132 | −20.987 | −25.118 |
| 0.000 | 40.000 | 2.556 | −11.638 | −14.195 |
| 0.000 | −30.000 | 1.599 | −5.382 | −7.281 |
| 0.000 | −20.000 | 1.825 | −1.291 | −3.116 |
| 0.000 | −10.000 | 1.808 | 1.041 | −0.767 |
| 0.000 | 0.000 | 1.800 | 1.800 | 0.000 |
| 0.000 | 10.000 | 1.808 | 1.041 | −0.767 |
| 0.000 | 20.000 | 1.825 | −1.291 | −3.116 |
| 0.000 | 30.000 | 1.899 | −5.382 | −7.281 |
| 0.000 | 40.000 | 2.556 | −11.638 | −14.195 |
| 0.000 | 50.000 | 4.132 | −20.987 | −25.118 |

Finally, it is to be understood that various other modifications and/or alterations may be made without departing from the spirit of the present invention as outlined herein.

We claim:

1. An optical lens element adapted for mounting in a frame of the wrap-around type, the lens element including a front and back surface capable of providing an optical zone, and a peripheral temporal zone which includes a prismatic correction to improve the overall field of vision of the wearer.

2. An optical lens element according to claim 1, wherein the prismatic correction is such that, in use, the wearer is provided with an increased awareness of objects and a substantially improved perception of the correct object location.

3. An optical lens element according to claim 2, wherein the placement and/or degree of application of the prismatic correction in the peripheral temporal zone is such that any perception by wearers, in use, of peripheral image distortion or motion/vestibular effects is reduced or eliminated.

4. An optical lens element according to claim 1, wherein the prismatic correction is such that the horizontal component of the prism reduces smoothly from base-nasal values to a substantially zero value across the peripheral temporal zone.

5. An optical lens element according to claim 4, wherein the point of maximum base-nasal prism is at or near the boundary of the optical zone.

6. An optical lens element according to claim 5, wherein the horizontal component of the prism, as measured normal to one of the lens surfaces, reduces smoothly from the maximum base-nasal prism value an amount in the range of 0.1 to 2.5 prism dioptre, at the temporal extremity of the lens element.

7. An optical lens element according to claim 6, wherein the reduction in base-nasal prism is in the range of 0.75 to 2.0 prism dioptre.

8. An optical lens element according to claim 7, wherein the reduction in base-nasal prism is in the range of 1.3 to 1.9 prism dioptre.

9. An optical tens element according to claim 1, wherein the lens element further includes a secondary prismatic correction in the optical zone to assist in ensuring that the primary line of sight is undisturbed, with the lens element in the as-worn position.

10. An optical lens element according to claim 1, wherein the lens element further includes a surface correction in the optical zone to enhance vision by reducing the off-axis blur.

11. An optical lens element according to claim 10, wherein the front and/or back surface is an aspheric or atoric surface selected to minimise optical errors including astigmatic or power errors resulting in off-axis blur.

12. An optical lens element according to claim 10, wherein the lens element further includes a secondary prismatic correction in the optical zone to assist in ensuring that the primary line of sight is undisturbed, with the lens element in the as-worn position.

13. An optical lens element according to claim 12, wherein the secondary prismatic correction is a base-nasal prismatic correction applied to the front and/or back surface.

14. An optical lens element according to claim 13, wherein the front and back surfaces of the lens element are tilted with respect to one another at the lens centre such that, when the lens element is in the as-worn condition, the primary line of sight undergoes substantially no angular deviation in a horizontal plane as it passes through the lens element.

15. An optical lens element according to claim 14, wherein the back surface is tilted relative to the front surface to introduce a base nasal prismatic correction of approximately 0.36 D when assessed normal to the surfaces for an 8 base polycarbonate lens.

16. An optical lens element according to claim 1, wherein the optical zone includes at least those portions of the lens that are used during eye rotations of up to 50° on the temporal side, up to 45° on the nasal side, and up to 30° vertically up and down from the primary line of sight, with the lens element in the as-worn position.

17. An optical lens element according to claim 1, wherein the lens element is adapted for mounting in a frame of the wrap-around or shield type, such that the lens is rotated temporally about a vertical axis through the optical centre thereof.

18. An optical lens element according to claim 1, wherein the lens element is adapted for mounting in a frame of the wrap-around or shield type, such that the lens is decentred to displace its optical axis from the line of sight while maintaining parallelism between the two in a horizontal plane.

19. An optical lens element according to claim 1, wherein the lens element is adapted for mounting in a frame of the wrap-around or shield type, such that the lens is both decentred and rotated temporally about a vertical axis through the design centre thereof.

20. An optical lens element according to claim 1, wherein the optical zone is a generally piano zone where the refractive power is approximately zero.

21. An optical lens element according to claim 1, which is an ophthalmic lens.

22. An ophthalmic lens according to claim 21, wherein the lens is a single vision, bi-focal or progressive lens.

23. An optical lens element adapted for mounting in a frame of the wrap-around or shield type, the lens element including a front and back surface capable of providing an optical zone and a peripheral temporal zone;

the front and/or back surface in the peripheral temporal zone bearing a prismatic correction such that the horizontal component of prism varies smoothly from base-nasal values to substantially zero across the zone;

the front and/or back surface in the optical zone bearing a base-nasal prismatic correction to at least partially compensate for prismatic errors in the primary line of sight of the wearer in the as-worn position.

24. An optical lens element according to claim 23, wherein the front and/or back surface further includes a surface correction to at least partially adjust for optical errors including astigmatic and mean power errors.

25. A laminate optical article adapted for mounting in a frame of the wrap-around or shield type, including a front lens wafer, and a complementary back lens wafer;

the front and back lens wafers of the laminate optical article defining an optical lens element including
a front and back surface capable of providing an optical zone and a peripheral temporal zone;
the front and/or back surface in the peripheral temporal zone bearing a prismatic correction such that the horizontal component of prism varies smoothly from base-nasal values to substantially zero across the zone;
the front and/or back surface in the optical zone bearing a base-nasal prismatic correction to at least partially compensate for prismatic errors in the primary line of sight of the wearer in the as-worn position.

26. A laminate optical article according to claim 25 wherein the front and/or back surface further includes a surface correction to at least partially adjust for optical errors including astigmatic and mean power errors.

* * * * *